(12) United States Patent
Nord et al.

(10) Patent No.: US 7,894,574 B1
(45) Date of Patent: Feb. 22, 2011

(54) APPARATUS AND METHOD PERTAINING TO DYNAMIC USE OF A RADIATION THERAPY COLLIMATOR

(75) Inventors: Janne Nord, Espoo (FI); Jarkko Peltola, Tuusula (FI)

(73) Assignee: Varian Medical Systems International AG, Zug (CH)

( * ) Notice: Subject to any disclaimer, the term of this patent is extended or adjusted under 35 U.S.C. 154(b) by 0 days.

(21) Appl. No.: 12/564,544

(22) Filed: Sep. 22, 2009

(51) Int. Cl.
*A61N 5/10* (2006.01)
(52) U.S. Cl. ...................................................... 378/65
(58) Field of Classification Search ............... 378/4, 378/19, 62, 64, 65, 147–155
See application file for complete search history.

(56) References Cited

U.S. PATENT DOCUMENTS

| 7,162,008 B2 | 1/2007 | Earl et al. | |
|---|---|---|---|
| 7,333,591 B2 | 2/2008 | Earl et al. | |
| 2004/0184578 A1 * | 9/2004 | Nakano | 378/65 |
| 2006/0256915 A1 | 11/2006 | Otto et al. | |
| 2008/0144772 A1 | 6/2008 | Yi et al. | |
| 2008/0226030 A1 | 9/2008 | Otto | |
| 2008/0298550 A1 | 12/2008 | Otto | |
| 2009/0116616 A1 * | 5/2009 | Lu et al. | 378/65 |

FOREIGN PATENT DOCUMENTS

| WO | 2008011725 A1 | 1/2008 |
|---|---|---|
| WO | 2008130634 A1 | 10/2008 |

OTHER PUBLICATIONS

Yi et al., "A Dose Rate Modulated Tracking Radiation Therapy System and Method," U.S. Appl. No. 60/874,678, filed Dec. 14, 2006; 23 pages.
Wang et al., "Arc-Modulated Radiation Therapy (AMRT): A Single Arc Form of Intensity-Modulated Arc Therapy," Physics in Medicine and Biology 53 (2008); 13 pages; IOP Publishing.

* cited by examiner

*Primary Examiner*—Irakli Kiknadze
(74) *Attorney, Agent, or Firm*—Fitch, Even, Tabin & Flannery

(57) ABSTRACT

A radiation-therapy treatment-facilitation platform (200) provides (101) treatment-plan information regarding a plurality of different angles of exposure to employ when administering radiation therapy to a given target volume (203). This treatment-plan information is then used (103) to determine corresponding, and differing, aperture configuration for a second collimator (207) that is disposed between a source (201) for the radiation-therapy beam (202) and a multileaf collimator (206). By one approach, this second collimator is dynamically used when administering the radiation therapy for at least some of the differing angles of exposure. These teachings will optionally accommodate also providing (102) form information regarding the target volume that is used, along with the aforementioned treatment-plan information, to determine the aperture settings for the second collimator.

27 Claims, 4 Drawing Sheets

FIG. 7  FIG. 8

APPARATUS AND METHOD PERTAINING TO DYNAMIC USE OF A RADIATION THERAPY COLLIMATOR

TECHNICAL FIELD

This invention relates generally to administering radiation therapy to target volumes and more particularly to the use of treatment-plan information in these regards.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Collimators are often used to restrict and form the radiation-therapy beam. Many collimators have a fixed aperture. Other collimators have an aperture that can be adjusted in one or more dimension. Adjustable apertures permit, to at least some degree, customization of the radiation-therapy beam's cross section to thereby attempt to better match the requirements of a given target volume. Multileaf collimators are an example of such a component. Multileaf collimators are comprised of a plurality of individual parts (known as "leaves") that are formed of a high atomic numbered material (such as tungsten) that can move independently in and out of the path of the radiation-therapy beam in order to selectively block the beam.

It is also known to employ more than one collimator in conjunction with a single radiation-therapy beam. In a not untypical application setting, for example, the radiation source often has a primary collimator comprising shielding that essentially completely surrounds the source save for an output aperture (which is often circular in shape). A second collimator (sometimes referred to as a "jaws") then serves to generally shape the beam while a downstream multileaf collimator then more specifically customizes the cross-section of the beam as described above.

Depending upon the specifics of a given target volume and/or the characteristics of a given treatment paradigm, prior art approaches in these regards can yield satisfactory results. In other cases, however, there is considerable room for improvement. In some cases, for example, these prior art approaches do not necessarily ensure an appropriately shaped beam at all times during a treatment session. In other cases, these prior art approaches do not yield optimum results within the time available for practical administration of the radiation therapy to a given patient.

BRIEF DESCRIPTION OF THE DRAWINGS

The above needs are at least partially met through provision of the apparatus and method pertaining to dynamic use of a radiation therapy collimator described in the following detailed description, particularly when studied in conjunction with the drawings, wherein:

FIG. 7 comprises a front-elevational schematic view as configured in accordance with various embodiments of the invention; and FIG. 8 comprises a front-elevational schematic view as configured in accordance with various embodiments of the invention.

Figure 1:
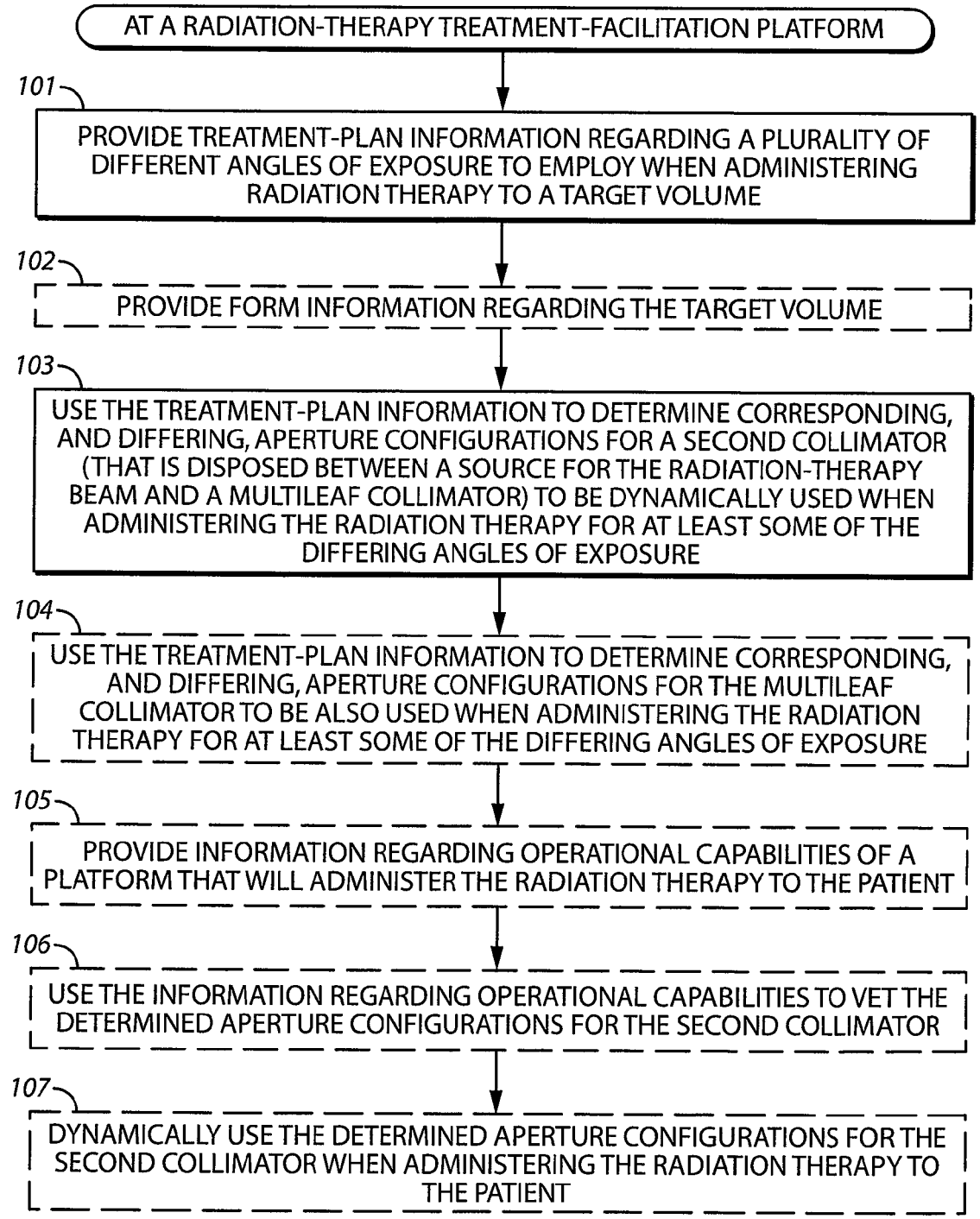
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a radiation-therapy treatment-facilitation platform can be employed to provide treatment-plan information regarding a plurality of different angles of exposure to employ when administering radiation therapy to a given target volume. This treatment-plan information is then used to determine corresponding, and differing, aperture configuration for a second collimator that is disposed between a source for the radiation-therapy beam and a multileaf collimator. By one approach, this second collimator is dynamically used when administering the radiation therapy for at least some of the differing angles of exposure.

By one approach, these teachings will further optionally accommodate also providing form information regarding the target volume. This form information can then be used, along with the aforementioned treatment-plan information, to determine the aperture settings for the second collimator. This form information can comprise, as one example, information regarding a particular form factor of the target volume as corresponds to each of the differing angles of exposure.

Those skilled in the art will appreciate that, if desired, this form information can also be employed to determine aperture configurations for the multileaf collimator as well. In such a case, and again if desired, these determined aperture configurations for the multileaf collimator can themselves be used to determine the aforementioned aperture configurations for the second collimator.

So configured, those skilled in the art will recognize and appreciate that these teachings will facilitate the formation and usage of a radiation-therapy beam that is, in many application settings, more appropriately conformal to a given target volume than is presently attainable using prior art techniques. It will further be understood and appreciated that these improved results are attained in a manner that will well accommodate the use of modern radiation-therapy treatments such as arc therapy. In particular, these teachings are applicable in application settings where the treatment-administration components remain in relatively constant motion. These teachings are well suited to use with many existing radiation-treatment platforms and it will further be appreciated that these approaches are highly scalable and can be employed in a wide variety of application settings with a wide variety of differing target volumes.

These and other benefits may become clearer upon making a thorough review and study of the following detailed description. Referring now to the drawings, and in particular to FIG. 1, an illustrative process that is compatible with many of these teachings will now be presented. In this illustrative example, a radiation-therapy treatment-facilitation platform carries out this process 100. Those skilled in the art will recognize that such a radiation-therapy treatment-facilitation platform can comprise, for example, a Treatment Planning System (TPS), the radiation-therapy delivery system itself, or some combination of both. For the sake of illustration, it will be presumed that the radiation therapy at issue comprises arc therapy as is known in the art. Those skilled in the art will recognize and understand that this example is intended to serve only in an illustrative capacity and is not intended to comprise an exhaustive listing of all possibilities in this regard.

This process 100 includes the step 101 of providing treatment-plan information regarding a plurality of different angles of exposure to employ when administering the radiation therapy to a target volume (such as a tumor located within a patient). This can comprise, for example, various dosages that are to be applied during a continuous exposure of the target volume to a radiation-therapy beam as relative motion between the beam source and the target volume occurs. (Those skilled in the art will recognize and understand that this reference to "providing" such information can comprise creating such information in the first instance (in whole or in part) or receiving such information from another source (for example, from another system component, a memory, or the like).) By one typical approach, for example, the beam source moves in an arc along a corresponding track around the patient to achieve this relative motion. Treatment plans are well known in the art and do not require further elaboration here.

If desired, this process 100 will also optionally include the step 102 of providing form information regarding the target volume. The specifics of this form information can of course vary with the needs or requirements of a given application setting. By one approach, this form information can comprise one or more spatial dimensions as pertain to the target volume. This can include, but it is not limited to, length dimensions, width dimensions, depth dimensions, shape characterizations, and so forth. Often the three dimensional shape of target has been defined. In such a case the shape information can comprise, for example, a set of contours or a three-dimensional triangle mesh as are known in the art.

In any event, this process 100 then provides the step 103 of using the treatment-plan information to determine corresponding, and differing, aperture configurations for a second collimator (that is disposed between the source for the radiation-therapy beam and a multileaf collimator) that is to be dynamically used when administering the radiation therapy for at least some of these differing angles of exposure. (As used herein, this reference to a "second collimator" will be understood to refer to a collimator that is "second" in the sense of being supplemental to the multileaf collimator and that is located between the multileaf collimator and the radiation source. It will also be understood that this reference to a "second collimator" is not intended to include a primary collimator such as apertured shielding that comprises a part of the radiation source itself. The expression "dynamically used," in turn, shall be understood to refer to a use that occurs while the radiation-therapy beam is active and does not refer to a use that occurs while the radiation-therapy beam is off.)

When this process 100 includes the step 102 of also providing form information regarding the target volume, this step 103 of using the treatment-plan information to determine second collimator aperture settings can further comprise also using this form information when determining some or all of these aperture settings. This can comprise, for example, determining a particular form factor of the target volume as corresponds to each of at least some of the differing angles of exposure. As one illustrative example in this regard, this can comprise determining a particular aperture configuration for the second collimator that will best accommodate the particular form factor of the target volume for each of a plurality of the differing angles of exposure. So configured, the radiation-therapy beam can be dynamically coarsely shaped prior to being dynamically finely shaped by the downstream multileaf collimator.

By one approach, this step 103 can comprise directly using the aforementioned form information to determine the aperture configurations for the second collimator. In this case, for example, information regarding a particular dimension of the target volume could be used to directly calculate a corresponding useful dimension for the aperture configuration. By another approach this step 103 can comprise indirectly using such form information to determine these aperture configurations. In this case, and again only by way of illustrative example, the form information could be used to determine aperture configurations for the multileaf collimator and that information regarding the aperture configurations for the multileaf collimator then used to determine the aperture configurations for the second collimator. It would also be possible to combine these two approaches in various ways if desired.

As alluded to above, this process 100 will readily optionally accommodate, if desired, the step 104 of using the aforementioned treatment-plan information to also determine corresponding (and, again, differing) aperture configurations for the multileaf collimator to also be used when administering the radiation therapy for at least some of the planned differing angles of exposure. The use of such information for this specific purpose of course comprises a well-understood area of endeavor and requires no further elaboration here.

Those skilled in the art will understand that not all radiation-administration platforms are the same. Numerous variations can and do exist with respect to not only the power of the radiation-therapy beam but also with respect to such things as the initial dimensions or shape of the beam, the distance from the source of radiation to the target volume/patient, the speed at which the source of radiation and the target volume move with respect to one another during the treatment procedure, a range of adjustability as corresponds to the second collimator, the speed-of-adjustability as pertains to the second collimator, and so forth. It is therefore possible in a given application setting that the aperture configurations determined via this process 100 will be partially (or wholly) impractical when the physical requirements as correspond to those aperture configurations are not reasonably met by the platform that will administer the radiation therapy to the patient.

In such a case, if desired, this process 100 will optionally accommodate the step 105 of providing information regarding the operational capabilities of the platform that will administer the radiation therapy to the patient and the step 106 of then using that information to vet the determined aperture configurations for the second collimator. Such a step can comprise, as one example in these regards, determining whether a particular aperture configuration to be used for a particular one of the differing angles of exposure is in fact physically possible.

By one approach, when these steps reveal a corresponding problem an alert can be provided to end users of this process 100. By another approach, if desired, this process 100 can accommodate a self-healing approach. For example, this vetting step can further comprise, if desired, automatically modifying the determined aperture configurations to ensure that the determined aperture configurations are capable of being implemented by the platform that will administer the radiation therapy to the patient.

In any event, this process 100 will also optionally accommodate the step 107 of dynamically using the determined aperture configurations for the second collimator when actually administering the radiation therapy to the patient. It will be understood that this step does not necessarily require constantly changing the aperture configuration of the second collimator during the entire exposure process from start to finish. Instead, it will suffice if the second collimator's aperture configuration is dynamically changed during at least a portion of the exposure process as corresponds to a given treatment procedure.

Figure 2:
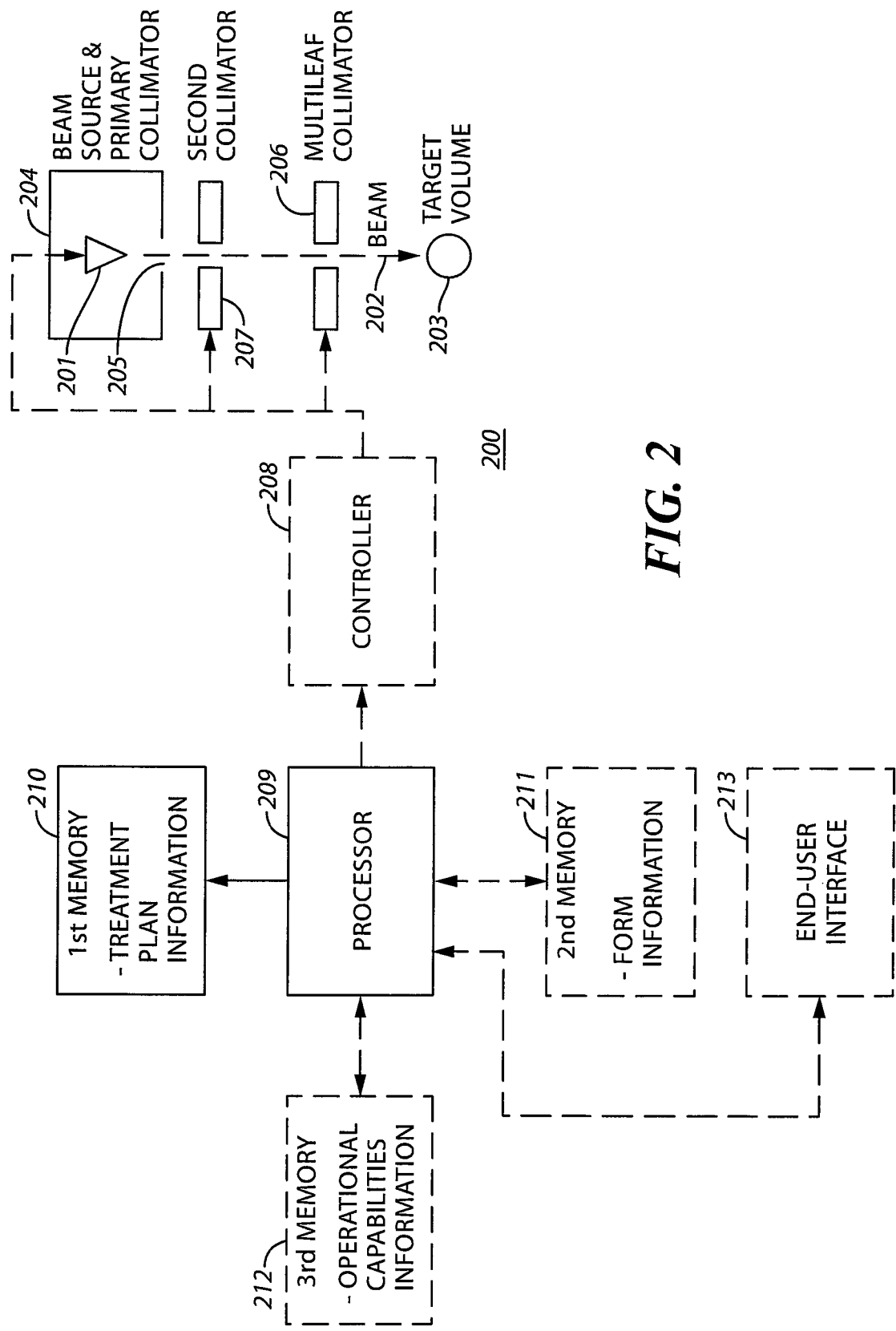
FIG. 2 comprises a block diagram as configured in accordance with various embodiments of the invention.

Those skilled in the art will appreciate that the above-described processes are readily enabled using any of a wide variety of available and/or readily configured platforms, including partially or wholly programmable platforms as are known in the art or dedicated purpose platforms as may be desired for some applications. Referring now to FIG. 2, an illustrative approach to such a platform will now be provided.

Figure 3:
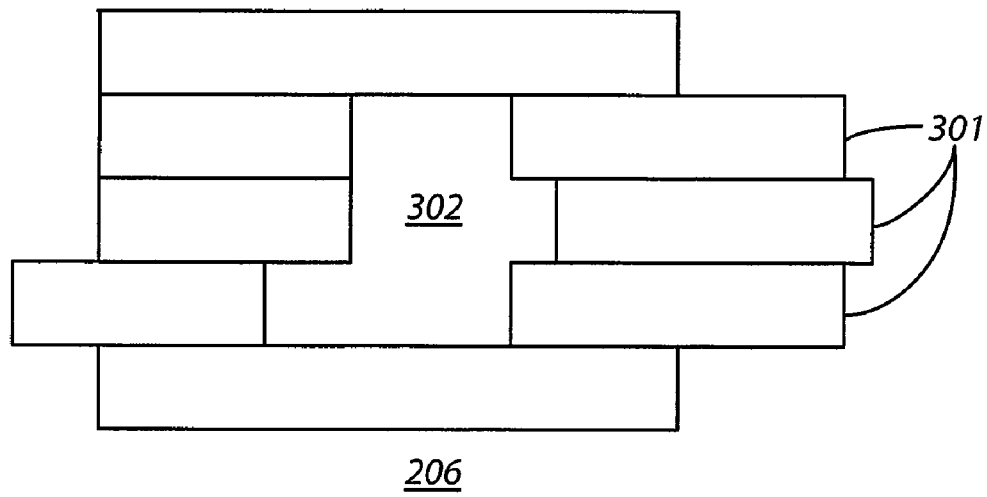
FIG. 3 comprises a front-elevational schematic view as configured in accordance with various embodiments of the invention.

This platform 200 comprises an apparatus to be used in the administration of radiation therapy to a target volume 203 of a patient using a radiation-therapy beam 202 and differing angles of exposure in conjunction with a multileaf collimator 206. Referring momentarily to FIG. 3, multileaf collimators 206 are known in the art and comprise a plurality of movable elements (i.e., "leaves") 301 that can be selectively positioned to thereby form a corresponding aperture 302 having a desired shape/configuration. In the illustrative example shown, these elements move horizontally. Those skilled in the art will understand that vertically-moving elements can be used in lieu of such an approach. It will also be understood that a considerably greater number of movable elements can be used as desired and that it would also be possible to use movable elements that differ in size with respect from one another if desired. Small motors (not shown) or the like are typically employed to effect the desired movement of these movable elements 301 (typically under the control of a corresponding controller 208 as shown in FIG. 2). As such multileaf collimators 206 are well known in the art, for the sake of brevity no further description of such a component will be provided here.

Referring again to FIG. 2, this illustrative platform 200 comprises a processor 209 and an operably coupled first memory 210. Here, this first memory 210 has treatment-plan information stored therein. This treatment-plan information can comprise the information regarding a plurality of different angles of exposure to employ (as described above) when administering the radiation therapy to the target volume 203.

The processor 209 can comprise a fixed-purpose hard-wired platform or can comprise a partially or wholly programmable platform. All of these architectural options are well known and understood in the art and require no further description here. This processor 209 can be configured (using, for example, corresponding programming as will be well understood by those skilled in the art) to carry out one or more of the steps, actions, or functions described herein. This can comprise, for example, configuring the processor 209 to access the first memory 210 and thereby acquire and use the treatment-plan information to determine the aforementioned corresponding, and differing aperture configurations for a second collimator 207 that is disposed between the multileaf collimator 206 and the beam source 201 (and any primary collimator 204/205 as may be associated with that beam source 201).

Figure 4:
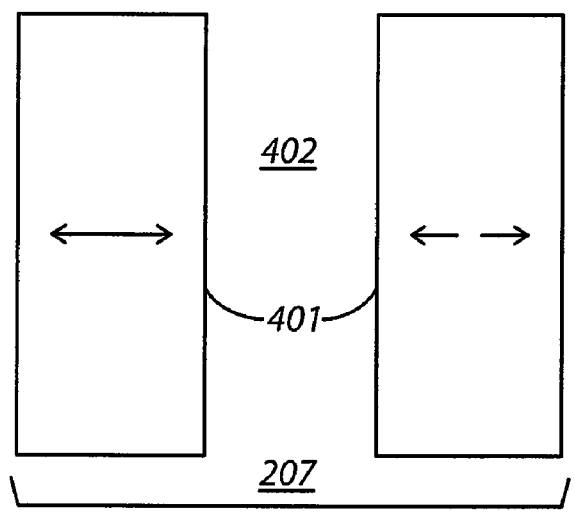
FIG. 4 comprises a front-elevational schematic view as configured in accordance with various embodiments of the invention.
Figure 5:
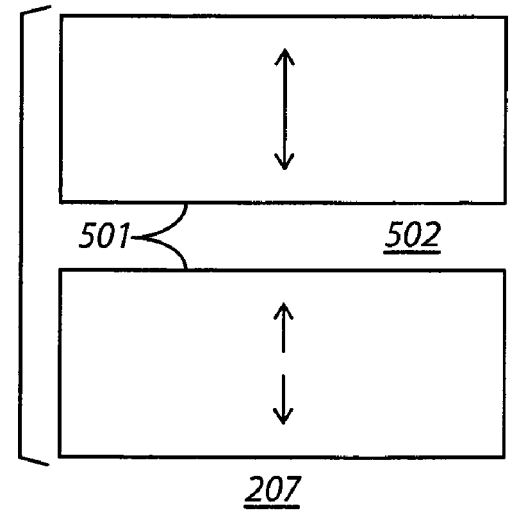
FIG. 5 comprises a front-elevational schematic view as configured in accordance with various embodiments of the invention.

This second collimator 207 can vary, of course, from one application setting to another. As one general illustration in this regard, and referring momentarily to FIG. 4, this second collimator 207 can comprise, in part, a pair of occluding jaws 401 that can move horizontally in order to create a larger, or smaller, aperture area 402. As another general illustration in this regard, and referring now momentarily to FIG. 5, this second collimator 207 can comprise, in lieu of the foregoing or in combination therewith, a pair of occluding jaws 501 that can move vertically in order to again create a larger, or smaller, aperture area 502. As with the multileaf collimator 206, the materials that comprise these jaws is highly absorptive of the beam's energy. Tungsten, for example, is often employed for such purposes.

These moving elements of the second collimator 207 can again be moved using corresponding motors (or other motive means of choice) (not shown) under the control of the aforementioned controller 208. So configured, these moving elements can be moved during the course of administering the radiation-therapy beam 202 to the target volume 203 under the control of the controller 208. Towards this end, if desired, the processor 209 can be operably coupled to this controller 208 to permit the former to provide the latter with the aforementioned aperture configuration information for the second collimator 207 to be dynamically used when effecting the treatment plan via the radiation-exposure platform. When the processor 209 comprises a part of a stand-alone Treatment Planning System, the processor 209 and the controller 208 will likely comprise discrete physical components. When the processor 209 comprises a part of the delivery system itself, the processor 209 and the controller 208 may comprise a shared enabling platform.

As described above, these teachings will accommodate using form information regarding the target volume when determining second collimator aperture configurations. To facilitate such functionality, if desired, this platform 200 can also comprise a second memory 211 to store such form information. Similarly, if desired, this platform 200 can also optionally comprise a third memory 212 to contain operational capabilities information as pertains to the delivery system. As noted earlier, this information can be utilized to vet the determined second collimator aperture configurations against the physical capabilities of the delivery system itself. It will be understood that the memory components shown can comprise a plurality of memory elements (as is suggested by the illustration) or can be comprised of a single memory element.

Those skilled in the art will recognize and understand that such an apparatus 200 may be comprised of a plurality of physically distinct elements as is suggested by the illustration shown in FIG. 2. It is also possible, however, to view this illustration as comprising a logical view, in which case one or more of these elements can be enabled and realized via a shared platform (excluding, of course, the various collimators which comprise discrete physical components).

Figure 6:
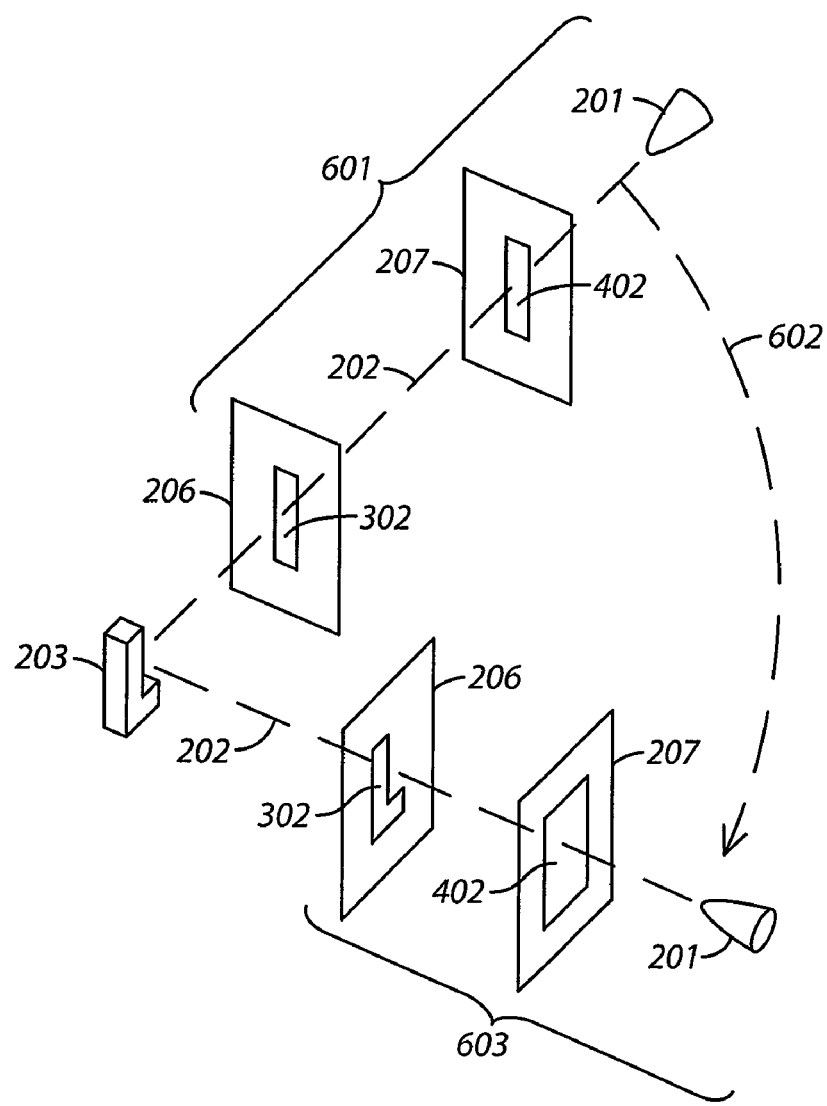
FIG. 6 comprises a perspective schematic view as configured in accordance with various embodiments of the invention.
Figure 6:
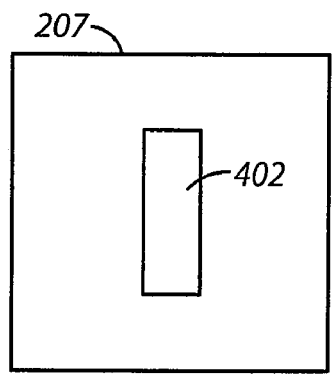
Figure 6:
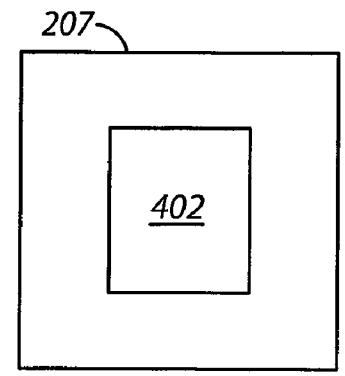

For the sake of illustration, and with no intention of suggestion any limitations in these regards, a simple example will now be presented. Referring now to FIG. 6, a target volume 203 appears as a thin upright rectangle to the radiation-therapy beam source 201 at a first angle of exposure 601. Here, form information regarding this presented shape of the target volume 203 is used as per these teachings to configure the aperture 402 of the second collimator 207 to itself comprise a thin upright rectangle (shown as well in FIG. 7). The aperture 302 for the multileaf collimator 206 is also similarly configured. So configured, the radiation-therapy beam 202 is well shaped with respect to the form of the target volume 203 at this angle of exposure 601.

With continued reference to FIG. 6, as the beam source 201 and the target volume 203 move (as indicated by the phantom line that is denoted by reference numeral 602)) to a new angle of exposure 603, the shape of the target volume 203 as presented to the beam source 201 changes. In this illustrative example, the target volume 203 now presents itself as an L-shaped object. The aperture 302 for the multileaf collimator 206 can accordingly assume an L shape. Such a shape is not precisely attainable by the second collimator 207. Nevertheless, as per these teachings, the second collimator's aperture 207 can be automatically configured as a wider rectangle (shown as well in FIG. 8). This shape is wide enough to match the bottom width of the L-shaped target volume 203, but narrow enough to absorb portions of the beam 202 that are beyond this boundary.

So configured, a radiation-therapy beam can be more reliably shaped to accommodate the specifics of a given treatment setting. At the same time, these teachings can be implemented in a relatively cost-effective manner. Those skilled in the art will recognize and appreciate that these teachings are readily implementable using already-fielded equipment and further that these teachings are highly scalable and can be employed in a wide variety of application settings.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method for use in administering radiation therapy to a target volume of a patient using a radiation-therapy beam and differing angles of exposure in conjunction with a multileaf collimator, comprising:
   at a radiation-therapy treatment-facilitation platform:
   providing treatment-plan information regarding a plurality of different angles of exposure to employ when administering the radiation therapy to the target volume;
   using the treatment-plan information to determine corresponding, and differing, aperture configurations for a second collimator that is disposed between a source for the radiation-therapy beam and the multileaf collimator to be dynamically used when administering the radiation therapy for at least some of the differing angles of exposure.

2. The method of claim 1 further comprising;
   providing form information regarding the target volume; and wherein using the treatment-plan information to determine the corresponding, and differing, aperture configurations for the second collimator comprises using the treatment-plan information and the form information to determine the corresponding, and differing, aperture configurations for the second collimator.

3. The method of claim 2 wherein using the treatment-plan information and the form information comprises, at least in part, determining a particular form factor of the target volume as corresponds to each of at least some of the differing angles of exposure.

4. The method of claim 3 wherein using the treatment-plan information and the form information further comprises, at least in part, determining a particular aperture configuration for the second collimator as will best accommodate the particular form factor of the target volume for each of the at least some of the differing angles of exposure.

5. The method of claim 2 wherein using the treatment-plan information and the form information to determine the corresponding, and differing, aperture configurations for the second collimator comprises directly using the form information to determine the aperture configurations.

6. The method of claim 2 wherein using the treatment-plan information and the form information to determine the corresponding, and differing, aperture configurations for the second collimator comprises indirectly using the form information to determine the aperture configurations.

7. The method of claim 6 wherein indirectly using the form information to determine the aperture configurations comprises:
   using the form information to determine aperture configurations for the multileaf collimator;
   using information regarding the aperture configurations for the multileaf collimator to determine the aperture configurations for the second collimator.

8. The method of claim 1 further comprising:
   dynamically using the determined aperture configurations for the second collimator when administering the radiation therapy to the patient.

9. The method of claim 1 further comprising:
   using the treatment-plan information to determine corresponding, and differing, aperture configurations for the multileaf collimator to be also used when administering the radiation therapy for at least some of the differing angles of exposure.

10. The method of claim 1 further comprising:
    providing information regarding operational capabilities of a platform that will administer the radiation therapy to the patient;
    using the information regarding the operational capabilities to vet the determined aperture configurations for the second collimator.

11. The method of claim 10 wherein vetting the determined aperture configurations for the second collimator comprises, at least in part, modifying the determined aperture configurations to ensure that the determined aperture configurations are capable of being implemented by the platform that will administer the radiation therapy to the patient.

12. The method of claim 11 further comprising:
    using the treatment-plan information to determine corresponding, and differing, aperture configurations for the multileaf collimator to be also used when administering the radiation therapy for at least some of the differing angles of exposure.

13. The method of claim 12 further comprising:
dynamically using the determined aperture configurations for the second collimator and the multileaf collimator when administering the radiation therapy to the patient.

14. The method of claim 1 wherein the radiation therapy comprises arc therapy.

15. An apparatus for use in administering radiation therapy to a target volume of a patient using a radiation-therapy beam and differing angles of exposure in conjunction with a multileaf collimator, comprising:
a first memory having treatment-plan information regarding a plurality of different angles of exposure to employ when administering the radiation therapy to the target volume stored therein;
a processor operably coupled to the first memory and being configured to use the treatment-plan information to determine corresponding, and differing, aperture configurations for a second collimator that is disposed between a source for the radiation-therapy beam and the multileaf collimator and that is to be dynamically used when administering the radiation therapy for at least some of the differing angles of exposure.

16. The apparatus of claim 15 further comprising:
a second memory having form information regarding the target volume stored therein;
and wherein the processor is also operably coupled to the second memory and is further configured to use the treatment-plan information to determine corresponding, and differing, aperture configurations for a second collimator by using the treatment-plan information and the form information to determine the corresponding, and differing, aperture configurations for the second collimator.

17. The apparatus of claim 16 wherein the processor is configured to use the treatment-plan information and the form information by, at least in part, determining a particular form factor of the target volume as corresponds to each of at least some of the differing angles of exposure.

18. The apparatus of claim 17 wherein the processor is configured to use the treatment-plan information and the form information by, at least in part, determining a particular aperture configuration for the second collimator as will best accommodate the particular form factor of the target volume for each of the at least some of the differing angles of exposure.

19. The apparatus of claim 15 wherein the processor is configured to:
dynamically use the determined aperture configurations for the second collimator when administering the radiation therapy to the patient.

20. The apparatus of claim 15 wherein the processor is configured to:
use the treatment-plan information to determine corresponding, and differing, aperture configurations for the multileaf collimator to be also dynamically used when administering the radiation therapy for at least some of the differing angles of exposure.

21. The apparatus of claim 15 further comprising:
a third memory having information regarding operational capabilities of a platform that will administer the radiation therapy to the patient stored therein;
and wherein the processor is configured to use the information regarding the operational capabilities to vet the determined aperture configurations for the second collimator.

22. The apparatus of claim 21 wherein the processor is configured to vet the determined aperture configurations for the second collimator by, at least in part, modifying the determined aperture configurations to ensure that the determined aperture configurations are capable of being implemented by the platform that will administer the radiation therapy to the patient.

23. The apparatus of claim 22 wherein the processor is configured to:
use the treatment-plan information to determine corresponding, and differing, aperture configurations for the multileaf collimator to be also dynamically used when administering the radiation therapy for at least some of the differing angles of exposure.

24. The apparatus of claim 23 wherein the processor is configured to:
dynamically use the determined aperture configurations for the second collimator and the multileaf collimator when administering the radiation therapy to the patient.

25. The apparatus of claim 15 wherein the radiation therapy comprises arc therapy.

26. An apparatus for use in administering radiation therapy to a target volume of a patient using a radiation-therapy beam and differing angles of exposure in conjunction with a multileaf collimator and a second collimator that is disposed between a source for the radiation-therapy beam and the multileaf collimator, comprising:
a first memory having treatment-plan information regarding a plurality of different angles of exposure to employ when administering the radiation therapy to the target volume stored therein;
a processor operably coupled to the first memory and being configured to use the treatment-plan information to dynamically vary aperture configurations for the second collimator when administering the radiation therapy for at least some of the differing angles of exposure.

27. The apparatus of claim 26 wherein the radiation therapy comprises arc therapy.

* * * * *